(12) United States Patent
McCulloh et al.

(10) Patent No.: US 6,386,235 B1
(45) Date of Patent: May 14, 2002

(54) AMBULATORY CYLINDER RECHARGING AND DISPENSING VALVE

(75) Inventors: Kevin Gene McCulloh, Simi Valley; Oscar J. Sanchez, Bell Canyon, both of CA (US)

(73) Assignee: Chad Therapeutics, Chatsworth, CA (US)

(*) Notice: Subject to any disclaimer, the term of this patent is extended or adjusted under 35 U.S.C. 154(b) by 0 days.

(21) Appl. No.: 09/753,165

(22) Filed: Jan. 2, 2001

(51) Int. Cl.[7] .............................................. F16K 21/00
(52) U.S. Cl. ................................... 137/881; 128/205.24
(58) Field of Search ....................... 128/205.24; 137/881

(56) References Cited

U.S. PATENT DOCUMENTS

| | | |
|---|---|---|
| 4,535,767 A | 8/1985 | Tiep et al. |
| 4,612,928 A | 9/1986 | Tiep et al. |
| 5,134,886 A | 8/1992 | Ball |
| 5,354,361 A | 10/1994 | Coffield |
| 5,402,665 A | 4/1995 | Hart et al. |
| 5,566,713 A * | 10/1996 | Lhomer et al. ............. 137/613 |
| 5,755,224 A * | 5/1998 | Good et al. ............. 128/205.24 |
| 6,047,743 A * | 4/2000 | Byrd ............................ 141/18 |
| 6,116,242 A * | 9/2000 | Frye et al. ............. 128/205.24 |
| 6,148,841 A * | 11/2000 | Davidson ................. 137/68.23 |

* cited by examiner

*Primary Examiner*—John Fox
(74) *Attorney, Agent, or Firm*—Price and Gess

(57) ABSTRACT

An in-home stationary oxygen delivery system provides oxygen to patients by way of a standard oxygen concentration process and delivers the oxygen to a patient through industry standard ports such as the CGA-870 port. A unique fill nozzle is used to fill the ambulatory cylinders from the in-home oxygen concentration. A valve for the ambulatory cylinder provides a unique fill port for mating with the nozzle of the stationary unit while at the same time allowing the oxygen in the charged cylinder to be dispensed through a CGA-870 standard industry port. The valve utilizes check valves to prevent filling of the cylinders through the CGA-870 port.

9 Claims, 2 Drawing Sheets

AMBULATORY CYLINDER RECHARGING AND DISPENSING VALVE

BACKGROUND OF THE INVENTION

1. Field of the Invention

The present invention relates generally to improvements in valves for pressurized gas cylinders and more particularly pertains to new and improved oxygen cylinder charging and dispensing valves.

2. Description of Related Art

In-home healthcare oxygen concentrators and ambulatory oxygen cylinder systems are being utilized to provide oxygen to patients who require supplemental oxygen due to cardiopulmonary disease. In the United States, the Food and Drug Administration (FDA) regulates oxygen concentrators and ambulatory oxygen cylinders. The FDA requires that the ambulatory cylinders may be refilled by home healthcare providers that are required to follow United States Pharmacopoeia (USP) standard UN 1072. These cylinders are filled through a compressed gas association (CGA) 870 filling port which has become a standard in the industry. As a result, secondary devices that need to be attached to the cylinder, for example, a pressure regulating device or an oxygen conserving device are designed for attachment to the CGA-870 port.

The FDA, through its regulations, requires that in-home oxygen concentrators or other oxygen generating devices can not fill an ambulatory oxygen cylinder through a CGA-870 port. Only home healthcare providers who follow the USP UN 1072 standards may utilize the CGA-870 port to fill ambulatory oxygen cylinders. The FDA does allow oxygen concentrating devices to fill ambulatory oxygen cylinders but only through a unique filling port which is not compatible with the CGA-870 port. This requirement insures that the ambulatory oxygen cylinders will only contain gas produced by the oxygen-concentrating devices. Moreover, the unique fill port required must be labeled accordingly, i.e., for use only with oxygen-concentrating devices.

The CGA-870 post valves which are an industry standard are used extensively for portable oxygen cylinders. Leading manufacturers of such post valves are the Sherwood Division of Harsco Corporation of Lockport, N.Y., Thermo Valves Corporation of Santa Rosa, Calif. and Condon Manufacturing Co., Inc. of Springfield, Mass. These CGA-870 post valves permit dispensing and charging of the cylinder, through the valve. A large variety of attachments are available on the marketplace for these valves.

Because of the FDA requirement that oxygen concentrating devices such as are available for in-home stationary use cannot be made attachable to a CGA-870 port, the cylinders that are fillable by these in-home oxygen concentrators utilize a valve with a unique fill port. This valve with the unique fill port requires a special built-in regulator. An off-the-shelf regulator can not be used because these regulators are adapted to fit the CGA-870 port. Special built-in regulators multiply the cost of the cylinder valve, thereby increasing the cost of each ambulatory oxygen cylinder. Moreover, use of a unique fill port valve greatly reduces a patient's choices of attachments to the cylinder.

None of the prior art devices have solved the problem of addressing the FDA regulation that only a unique fill port is used on oxygen concentrating devices to fill ambulatory oxygen cylinders, while at the same time providing a CGA-870 port on the valve.

SUMMARY OF THE INVENTION

The present invention provides a valve assembly for attachment to an ambulatory oxygen cylinder which is adapted to connect to a high pressure source that delivers oxygen concentrated air to charge the cylinder through a unique fill port, while at the same time providing an industry standard CGA-870 output port. The valve assembly will not permit filling the cylinder through the CGA-870 port. The CGA-870 port is useable only to dispense oxygen from the cylinder.

BRIEF DESCRIPTION OF THE DRAWINGS

The exact nature of this invention as well as its objects and advantages will become readily apparent upon consideration of the following detailed description as illustrated in the accompanied drawings, in which like reference numerals designate like parts throughout the figures thereof and wherein.

DETAILED DESCRIPTION OF THE PREFERRED EMBODIMENTS

Figure 1:
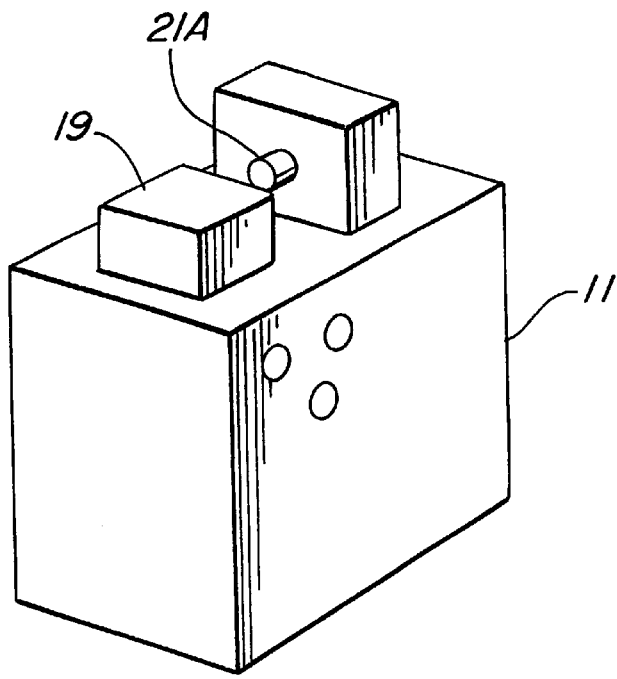
FIG. 1 is a prospective illustration of an in-home oxygen concentrator.

FIG. 1 illustrates a stationary oxygen system 11 which is typically used by patients who require supplemental oxygen due to cardiopulmonary disease, for example. These stationary oxygen systems 11 are typically oxygen concentrators and weigh approximately 70 lbs. or more. They typically produce flow rates of 0 to 3 liters per minute at a pressure of 6 psi of oxygen concentrated air when a patient is utilizing the stationary system for oxygen supplementation. The system may also be utilized to fill ambulatory oxygen cylinders 19 through a uniquely sized fill nozzle 21A. When the stationary system is operating as a fill station, it typically operates at a fill rate of one-half liter per minute, produces an oxygen concentrated gas of approximately 93% oxygen at a pressure of approximately 2,000 psi.

The ambulatory cylinders 19 may vary in size, from 40 to 248 liters, for example and are rated for at least 2,000 psi. These cylinders typically have a built-in regulator and vary in weight from 3 lbs. to 5½ lbs., for example. The in-home oxygen concentrator system 11 typically fills such cylinders from 1.3 to 8.3 hours.

Figure 2:
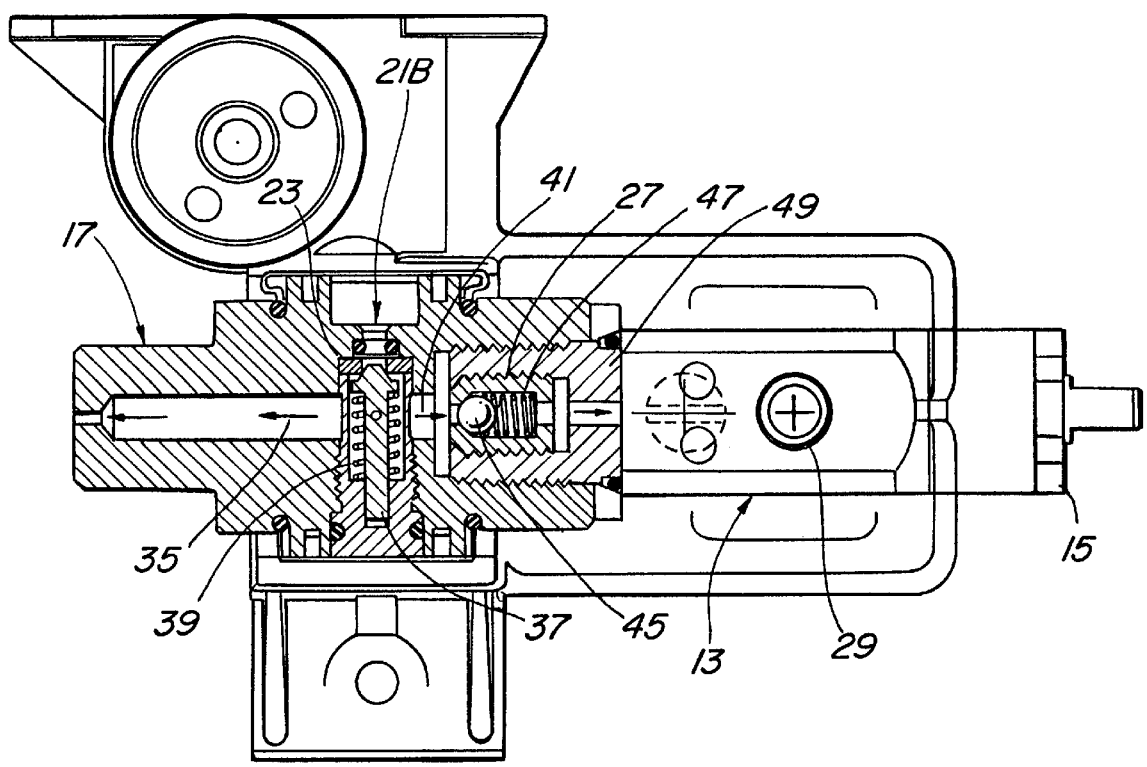
FIG. 2 is a cross-section plan view of a valve built according to the present invention.

As a result of the FDA requirement, the special fill nozzle 21A required by the FDA must mate with a matching fill port 21B on the valve 13 (FIGS. 2, 3) which attaches to the ambulatory cylinder 19 by way of a threaded cylinder attachment nozzle 17 (FIG. 2). The preferred structure of the ambulatory cylinder valve 13 is shown in FIG. 2. Once the cylinder valve 13 is attached to the cylinder by the threaded attachment post 17, valve 13 acts as a normal short post CGA-870 dispensing valve with ready attachment to CGA-870 compatible regulators or conserving devices by way of GCA-870 port 15.

Once the cylinder 19 is attached to the in-home oxygen concentrator 11 by way of valve 13, specifically the unique fill port 21B and fill nozzle 21A, the stationary system 11 supplies gas at about 2,000 psi to the cylinder 19 through a first check valve 23 to cylinder attachment port 17 in the flow direction 35. The ambulatory oxygen cylinder 19 cannot be filled through the CGA-870 port 15 even if it were attachable to the uniquely sized fill nozzle 21A on the in-home oxygen concentrator unit 11. A second check value 27 allows gas flow only in the direction 41. The unique fill port 21A–B with its male portion 21A located on the oxygen concentrator unit 11 and its female portion 21B located on the body of the valve 13, may be unique because of its diameter size, thread count, or any other arrangement that confines the connection of male portion 21A to female portion 21B, and prevents connection of a CGA nozzle to port 21B.

The inlet check valve 23 is essentially a piston 37 held in a closed position by a helical spring 39. The piston is moved to an open position allowing gas flow through the fill port 21B, into the body of valve 23 and out both of its outlets in the body causing flow in direction 35 and 41. An outlet valve 29 in gas flow path 41 prevents the high pressure oxygen concentrated air from exiting at GCA-870 port 15 during the fill process.

The second check valve 27 is located in the gas channel from the ambulatory cylinder 19 to the CGA-870 output port 15. The check valve 27 permits oxygen concentrated air flow 41 in the direction 49 when outlet valve 29 is open. The concentrated oxygen air flow will compress the spring 47 on which ball 45 rides. Any attempt to fill cylinder 19 through the CGA-870 port 15 will be prevented by ball check valve 27 which shuts off all gas flow in a direction opposite to outflow 41, 49.

Figure 3:
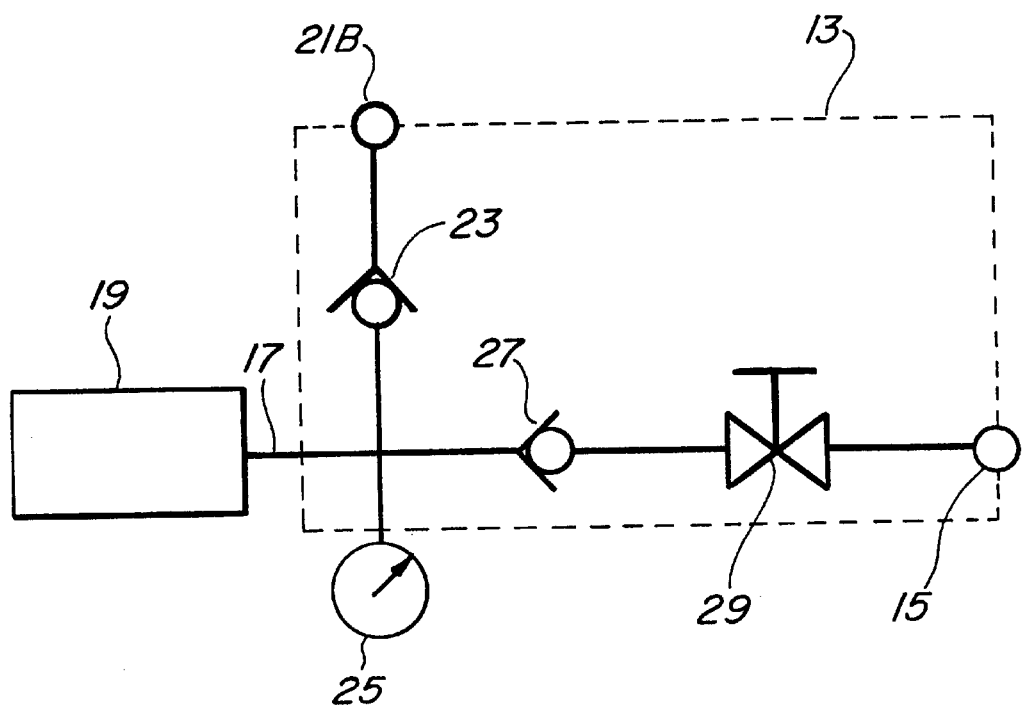
FIG. 3 is a schematic diagram showing the operation of the valve of FIG. 2.

The operation of the valve 13 is more easily understood by reference to the diagram of FIG. 3. To start the filling process for ambulatory oxygen cylinder 19, outlet valve 29 is closed and valve 13 is connected to the output nozzle 21A by way of mating fill port 21B. High pressure oxygen gas then enters through unique fill port 21B into the body of valve 13 and through inlet check valve 23. Inlet check valve 23 prevents any gas present in ambulatory cylinder 19 from escaping cylinder 19, once the valve 13 is connected to the cylinder. After flowing past check valve 23, the oxygen flows into the cylinder 19. It continues to flow and fill the cylinder until adequate pressure, as indicated by pressure gauge 25 is reached. As long as outlet valve 29 remains closed, the oxygen stored in the cylinder 19 remains there, ready for use.

After filling, the cylinder 19 and valve 13 assembly can be disconnected from the fill nozzle 21A. A regulator or regulator and conserving device can be connected to the CGA-870 output port 15. In order to use the ambulatory oxygen cylinder, the patient would open the outlet valve 29 and gas will flow from the cylinder 19, through the outlet check valve 27, through the outlet valve 29, and out CGA-870 port 15 to the attached regulating device or similar apparatus being used by the patient.

As can be seen, the oxygen cylinder charging and dispensing valve of the present invention provides a CGA-870 port which may be connected to a variety of regulators and conserving devices adapted for such standardized connection while at the same time preventing filling of the cylinder through the CGA-870 port, and only permitting filling of the ambulatory cylinder through a unique mating fill port arrangement 21A–21B.

What is claimed is:

1. An oxygen charging and dispensing valve having a valve body, comprising:

a cylinder attachment port on the valve body for attachment to an oxygen cylinder;

a fill port on the valve body sized to fit a unique oxygen dispensing nozzle;

an outlet port on the valve body sized to industry standard; and a unidirectional valve in the body of the charging and dispensing valve permitting oxygen to only flow out the output port.

2. The oxygen cylinder charging and dispensing valve of claim 1 wherein said unidirectional valve comprises:

a first unidirectional valve located to only permit oxygen flow from the fill port to the cylinder attachment port; and a second unidirectional valve located to only permit oxygen flow from the attachment port to the outlet port.

3. The oxygen cylinder charging and dispensing valve of claim 1 wherein the outlet port is a CGA-870 port.

4. The oxygen cylinder charging and dispensing valve of claim 1 wherein the unidirectional valve is a spring loaded check valve.

5. The oxygen cylinder charging and dispensing valve of claim 2 wherein the outlet port is a CGA-870 port.

6. The oxygen cylinder charging and dispensing valve of claim 2 wherein the first unidirectional valve is a spring loaded check valve.

7. The oxygen cylinder charging and dispensing valve of claim 6 wherein the second unidirectional valve is a spring loaded ball check valve.

8. The oxygen cylinder charging and dispensing valve of claim 7 wherein the first unidirectional valve has one input and two outputs.

9. The oxygen cylinder charging and dispensing valve of claim 8 wherein the second unidirectional valve has one input and one output.

\* \* \* \* \*